(12) United States Patent
Lee et al.

(10) Patent No.: US 10,820,884 B2
(45) Date of Patent: Nov. 3, 2020

(54) ULTRASOUND DIAGNOSIS APPARATUS AND METHOD OF OPERATING THE SAME

(71) Applicant: SAMSUNG MEDISON CO., LTD., Hongcheon-gun (KR)

(72) Inventors: Kwang-hee Lee, Hongcheon-gun (KR); Jun-sang Yoo, Hongcheon-gun (KR); Gil-ju Jin, Hongcheon-gun (KR); Eun-ho Yang, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 1143 days.

(21) Appl. No.: 14/971,066

(22) Filed: Dec. 16, 2015

(65) Prior Publication Data
US 2016/0166233 A1 Jun. 16, 2016

(30) Foreign Application Priority Data
Dec. 16, 2014 (KR) .................. 10-2014-0181612

(51) Int. Cl.
*A61B 8/00* (2006.01)
*A61B 8/08* (2006.01)
*A61B 8/12* (2006.01)

(52) U.S. Cl.
CPC .......... *A61B 8/4254* (2013.01); *A61B 8/0866* (2013.01); *A61B 8/12* (2013.01);
(Continued)

(58) Field of Classification Search
None
See application file for complete search history.

(56) References Cited

U.S. PATENT DOCUMENTS 8,328,725 B2 12/2012 Anthony et al.
2004/0210136 A1 10/2004 Varghese et al.
(Continued)

FOREIGN PATENT DOCUMENTS

EP 0920833 A1 6/1999
JP 2000-271136 A 10/2000
(Continued)

OTHER PUBLICATIONS

Edwin R. Guzman, MD et al., "The natural history of a positive response to transfundal pressure in women at risk for cervical incompetence", American Journal of Obstetrics & Gynecology, vol. 176, No. 3, Mar. 1997, pp. 634-638 XP005140025A.
(Continued)

*Primary Examiner* — Bill Thompson
*Assistant Examiner* — Shahdeep Mohammed
(74) *Attorney, Agent, or Firm* — Sughrue Mion, PLLC

(57) ABSTRACT

Disclosed are an ultrasound diagnosis apparatus and a method of operating the same, which more accurately measure a cervix length. The ultrasound diagnosis apparatus includes a pressure measurer that measures a pressure value applied from a probe to a cervix, an image generator that scans an object to acquire an ultrasound image, a controller that determines whether a cervix line is included in the ultrasound image, acquires the measured pressure value, corresponding to the ultrasound image, as a first pressure value when the cervix line is included in the ultrasound image, and acquires a second pressure value for measuring a length of the cervix line, and an output unit that outputs pressure information based on at least one selected from the first pressure value and the second pressure value.

18 Claims, 16 Drawing Sheets

(52) U.S. Cl.
CPC ............ *A61B 8/4483* (2013.01); *A61B 8/463* (2013.01); *A61B 8/467* (2013.01); *A61B 8/485* (2013.01); *A61B 8/5207* (2013.01); *A61B 8/5223* (2013.01); *A61B 8/5292* (2013.01); *A61B 8/4444* (2013.01)

(56) References Cited

U.S. PATENT DOCUMENTS

| | | | | |
|---|---|---|---|---|
| 2008/0167581 | A1* | 7/2008 | Paltieli | A61B 5/1076 600/588 |
| 2010/0036243 | A1 | 2/2010 | Matsumura | |
| 2012/0083692 | A1 | 4/2012 | Stoll | |
| 2012/0232394 | A1* | 9/2012 | Toji | A61B 5/1075 600/443 |
| 2012/0302885 | A1* | 11/2012 | Yoo | A61B 8/08 600/443 |

FOREIGN PATENT DOCUMENTS

| | | |
|---|---|---|
| JP | 2006-238913 A | 9/2006 |
| JP | 2008-183097 A | 8/2008 |
| JP | 2009-136416 A | 6/2009 |
| WO | 2011/098783 A1 | 8/2011 |

OTHER PUBLICATIONS

Communication dated May 9, 2016, from the European Patent Office in counterpart European Application No. 15196167.9.

\* cited by examiner

ULTRASOUND DIAGNOSIS APPARATUS AND METHOD OF OPERATING THE SAME

RELATED APPLICATION

This application claims the benefit of Korean Patent Application No. 10-2014-0181612, filed on Dec. 16, 2014, in the Korean Intellectual Property Office, the disclosure of which is incorporated herein in its entirety by reference.

BACKGROUND

1. Field

One or more exemplary embodiments relate to an ultrasound diagnosis apparatus, a method of operating the same, and a computer-readable storage medium, and more particularly, to an ultrasound diagnosis apparatus, a method of operating the same, and a computer-readable storage medium, which measure pressure applied from a probe to an object in an ultrasound diagnosis and measure a length of a cervix line.

2. Description of the Related Art

Ultrasound diagnosis apparatuses transmit ultrasound signals generated by transducers of a probe to an object and receive ultrasound echo signals reflected from the object, thereby obtaining at least one image of an internal part of the object. In particular, ultrasound diagnosis apparatuses are used for medical purposes including observation of the interior of an object, detection of foreign substances, and diagnosis of damage to the object. Such ultrasound diagnosis apparatuses provide high stability, display images in real time, and are safe due to the lack of radioactive exposure, compared to X-ray apparatuses. Therefore, ultrasound imaging apparatuses are widely used together with other image diagnosis apparatuses.

In this context, when a pregnant woman has an incompetent cervix or a cervix length (CL) of the pregnant woman is short, there is a risk of premature labor. Particularly, when a cervix length is equal to or less than 2.5 cm, a risk of premature labor is determined. However, it is difficult for an ultrasound diagnosis apparatus of the related art to measure a cervix length, which is an indicator of parturition or natural premature labor. For example, to perform an ultrasound diagnosis on a cervix, if a certain pressure or more is not applied to the cervix, it is difficult to acquire an image capable of measuring the cervix. Also, if too high pressure is applied to the cervix, the cervix deforms, and for this reason, it is difficult to measure an accurate length. Therefore, a user applies appropriate pressure to the cervix depending on an experience of a doctor, and then, measures the cervix. Due to such problems, an inexperienced doctor has difficulties measuring the length of the cervix, and moreover, since pressures respectively applied to measured persons differ, a cervix length is often changed.

Therefore, it is required to develop an ultrasound diagnosis apparatus and a method of operating the same, which more accurately measure a cervix length.

SUMMARY

One or more exemplary embodiments include an ultrasound diagnosis apparatus and a method of operating the same, which more accurately measure a cervix length.

Additional aspects will be set forth in part in the description which follows and, in part, will be apparent from the description, or may be learned by practice of the presented exemplary embodiments.

According to one or more exemplary embodiments, an ultrasound diagnosis apparatus includes: a pressure measurer that measures a pressure value applied from a probe to a cervix; an image generator that scans an object to acquire an ultrasound image; a controller that determines whether a cervix line is included in the ultrasound image, acquires the measured pressure value, corresponding to the ultrasound image, as a first pressure value when the cervix line is included in the ultrasound image, and acquires a second pressure value for measuring a length of the cervix line; and an output unit that outputs pressure information based on at least one selected from the first pressure value and the second pressure value.

The image generator may acquire a plurality of ultrasound images from different positions of the probe, and the controller may compare the acquired plurality of ultrasound images to determine whether there is the cervix line.

The controller may detect a contour line from the ultrasound image by using at least one selected from a Sobel mask, a Prewitt mask, a Robert mask, and a Canny mask, and determine whether there is the cervix line, based on the contour line.

The controller may acquire, as the pressure information, an arithmetic relationship between the first pressure value and the second pressure value.

The output unit may output the pressure information as at least one selected from a letter, a figure, a color, a sound, and vibration.

The ultrasound diagnosis apparatus may further include a user input unit that receives the second pressure value from a user.

The pressure measurer may include a variant that is disposed in front of a transducer of the probe, and the pressure measurer may measure the pressure value, based on a deformation degree of the variant which appears in the ultrasound image and an elastic coefficient of the variant.

The pressure measurer may include a pressure sensor that is disposed in the probe, and the pressure measurer may measure the pressure value, based on an output of the pressure sensor.

The pressure measurer may include a piezo element, and the pressure measurer may measure the pressure value, based on an electrical signal output from the piezo element.

The piezo element may be at least one of a plurality of transducers included in the probe.

According to one or more exemplary embodiments, an ultrasound diagnosis apparatus includes: a pressure measurer that measures a pressure value applied from a probe to a cervix; a data acquirer that scans an object to acquire ultrasound data; and a controller that measures a length of a cervix line from the ultrasound data, and performs control to display a relationship between a change amount of the measured pressure value and a change amount of the length of the cervix line corresponding to the measured pressure value.

According to one or more exemplary embodiments, a method of operating an ultrasound diagnosis apparatus includes: measuring a pressure value applied from a probe to a cervix; scanning an object to acquire an ultrasound image; determining whether a cervix line is included in the ultrasound image; acquiring the measured pressure value, corresponding to the ultrasound image, as a first pressure value when the cervix line is included in the ultrasound image; acquiring a second pressure value for measuring a length of the cervix line; and outputting pressure information based on at least one selected from the first pressure value and the second pressure value.

The acquiring of the ultrasound image may include acquiring a plurality of ultrasound images from different positions of the probe, and the determining may include comparing the acquired plurality of ultrasound images to determine whether there is the cervix line.

The determining may include: detecting a contour line from the ultrasound image by using at least one selected from a Sobel mask, a Prewitt mask, a Robert mask, and a Canny mask; and determining whether there is the cervix line, based on the contour line.

The method may further include acquiring, as the pressure information, an arithmetic relationship between the first pressure value and the second pressure value.

The outputting may include outputting the pressure information as at least one selected from a letter, a figure, a color, a sound, and vibration.

The method may further include receiving the second pressure value from a user.

A variant may be disposed in front of a transducer of the probe, and the measuring of the pressure value may include measuring the pressure value, based on a deformation degree of the variant which appears in the ultrasound image and an elastic coefficient of the variant.

The probe may include a pressure sensor, and the measuring of the pressure value may include measuring the pressure value, based on an output of the pressure sensor.

The probe may include a piezo element, and the measuring of the pressure value may include measuring the pressure value, based on an electrical signal output from the piezo element.

According to one or more exemplary embodiments, a method of operating an ultrasound diagnosis apparatus includes: measuring a pressure value applied from a probe to a cervix; scanning an object to acquire ultrasound data; measuring a length of a cervix line from the ultrasound data; and displaying a relationship between a change amount of the measured pressure value and a change amount of the length of the cervix line corresponding to the measured pressure value.

According to one or more exemplary embodiments, a computer-readable recording medium storing a program according to an exemplary embodiment may implement the method of the ultrasound diagnosis apparatus.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
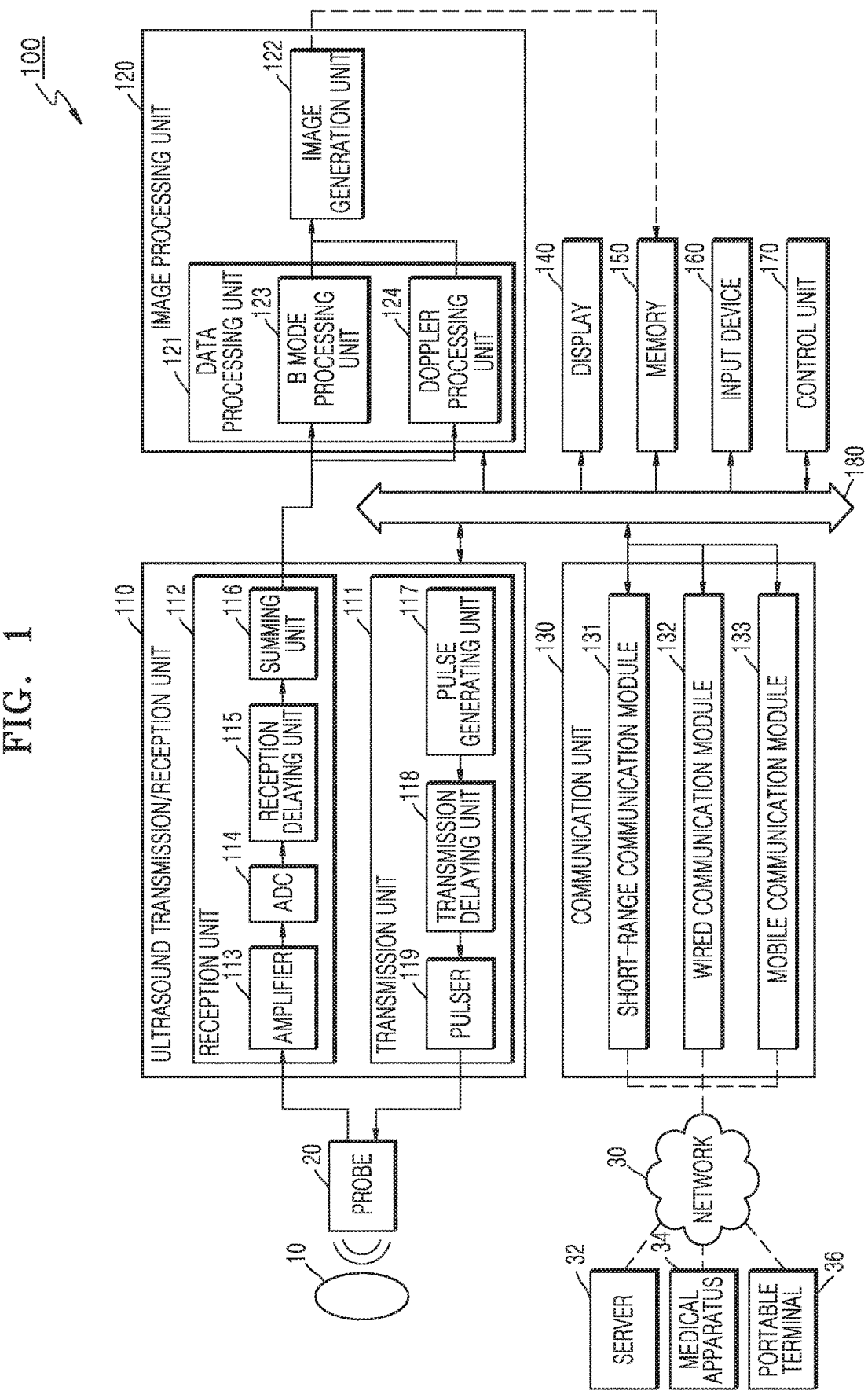
FIG. 1 is a block diagram illustrating a configuration of an ultrasound diagnosis apparatus according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the invention.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, heart, womb, brain, breast, or abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Embodiments of the invention now will be described more fully hereinafter with reference to the accompanying drawings, in which illustrative embodiments of the invention are shown.

FIG. 1 is a block diagram showing a configuration of an ultrasound diagnosis apparatus 100 according to an embodiment. Referring to FIG. 1, the ultrasound diagnosis apparatus 100 may include a probe 20, an ultrasound transceiver 110, an image processor 120, a communication module 130, a display 140, a memory 150, an input device 160, and a controller 170, which may be connected to one another via buses 180.

The ultrasound diagnosis apparatus 100 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 110 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound apparatus 100 by wire or wirelessly, and the ultrasound diagnosis apparatus 100 may include a plurality of probes 20 depending on an implementation type.

A transmitter 111 supplies a driving signal to the probe 20. The transmitter 110 includes a pulse generator 117, a transmission delaying unit 118, and a pulser 119. The pulse generator 117 generates pulses for forming transmission ultrasound waves based on a predetermined pulse repetition frequency (PRF), and the transmission delaying unit 118 delays the pulses by delay times necessary for determining transmission directionality. The pulses which have been delayed correspond to a plurality of piezoelectric vibrators included in the probe 20, respectively. The pulser 119 applies a driving signal (or a driving pulse) to the probe 20 based on timing corresponding to each of the pulses which have been delayed.

A receiver 112 generates ultrasound data by processing echo signals received from the probe 20. The receiver 120 may include an amplifier 113, an analog-to-digital converter (ADC) 114, a reception delaying unit 115, and a summing unit 116. The amplifier 113 amplifies echo signals in each channel, and the ADC 114 performs analog-to-digital conversion with respect to the amplified echo signals. The reception delaying unit 115 delays digital echo signals output by the ADC 124 by delay times necessary for determining reception directionality, and the summing unit 116 generates ultrasound data by summing the echo signals processed by the reception delaying unit 115. In some embodiments, the receiver 112 may not include the amplifier 113. In other words, if the sensitivity of the probe 20 or the capability of the ADC 114 to process bits is enhanced, the amplifier 113 may be omitted.

The image processor 120 generates an ultrasound image by scan-converting ultrasound data generated by the ultrasound transceiver 110 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 123 extracts B mode components from ultrasound data and processes the B mode components. An image generator 122 may generate an ultrasound image indicating signal intensities as brightness based on the extracted B mode components.

Similarly, a Doppler processor 124 may extract Doppler components from ultrasound data, and the image generator 122 may generate a Doppler image indicating a movement of an object as colors or waveforms based on the extracted Doppler components.

According to an embodiment, the image generator 122 may generate a three-dimensional (3D) ultrasound image via volume-rendering with respect to volume data and may also generate an elasticity image by imaging deformation of the object 10 due to pressure. Furthermore, the image generator 122 may display various pieces of additional information in an ultrasound image by using text and graphics. In addition, the generated ultrasound image may be stored in the memory 150.

A display 140 displays the generated ultrasound image. The display 140 may display not only an ultrasound image, but also various pieces of information processed by the ultrasound diagnosis apparatus 100 on a screen image via a graphical user interface (GUI). In addition, the ultrasound diagnosis apparatus 100 may include two or more displays 140 according to embodiments.

The communication module 130 is connected to a network 30 by wire or wirelessly to communicate with an external device or a server. The communication module 130 may exchange data with a hospital server or another medical apparatus in a hospital, which is connected thereto via a PACS. Furthermore, the communication module 130 may perform data communication according to the digital imaging and communications in medicine (DICOM) standard.

The communication module 130 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 130 may receive information about a diagnosis history or medical treatment schedule of a patient from a server and utilizes the received information to diagnose the patient. Furthermore, the communication module 130 may perform data communication not only with a server or a medical apparatus in a hospital, but also with a portable terminal of a medical doctor or patient.

The communication module 130 is connected to the network 30 by wire or wirelessly to exchange data with a server 32, a medical apparatus 34, or a portable terminal 36. The communication module 130 may include one or more components for communication with external devices. For example, the communication module 1300 may include a local area communication module 131, a wired communication module 132, and a mobile communication module 133.

The local area communication module 131 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 132 refers to a module for communication using electric signals or optical signals. Examples of wired communication techniques according to an embodiment may include communication via a twisted pair cable, a coaxial cable, an optical fiber cable, and an Ethernet cable.

The mobile communication module 133 transmits or receives wireless signals to or from at least one selected from a base station, an external terminal, and a server on a mobile communication network. The wireless signals may be voice call signals, video call signals, or various types of data for transmission and reception of text/multimedia messages.

The memory 150 stores various data processed by the ultrasound diagnosis apparatus 100. For example, the memory 150 may store medical data related to diagnosis of an object, such as ultrasound data and an ultrasound image that are input or output, and may also store algorithms or programs which are to be executed in the ultrasound diagnosis apparatus 100.

The memory 150 may be any of various storage media, e.g., a flash memory, a hard disk drive, EEPROM, etc. Furthermore, the ultrasound diagnosis apparatus 100 may utilize web storage or a cloud server that performs the storage function of the memory 150 online.

The input device 160 refers to a means via which a user inputs data for controlling the ultrasound diagnosis apparatus 100. The input device 160 may include hardware components, such as a keypad, a mouse, a touch pad, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 170 may control all operations of the ultrasound diagnosis apparatus 100. In other words, the controller 170 may control operations among the probe 20, the ultrasound transceiver 110, the image processor 120, the communication module 130, the display 140, the memory 150, and the input device 160 shown in FIG. 1.

All or some of the probe 20, the ultrasound transceiver 110, the image processor 120, the communication module 130, the display 140, the memory 150, the input device 160, and the controller 170 may be implemented as software modules. However, embodiments are not limited thereto, and some of the components stated above may be implemented as hardware modules. Furthermore, at least one selected from the ultrasound transceiver 110, the image processor 120, and the communication module 130 may be included in the controller 170. However, embodiments of the present invention are not limited thereto.

Figure 2:
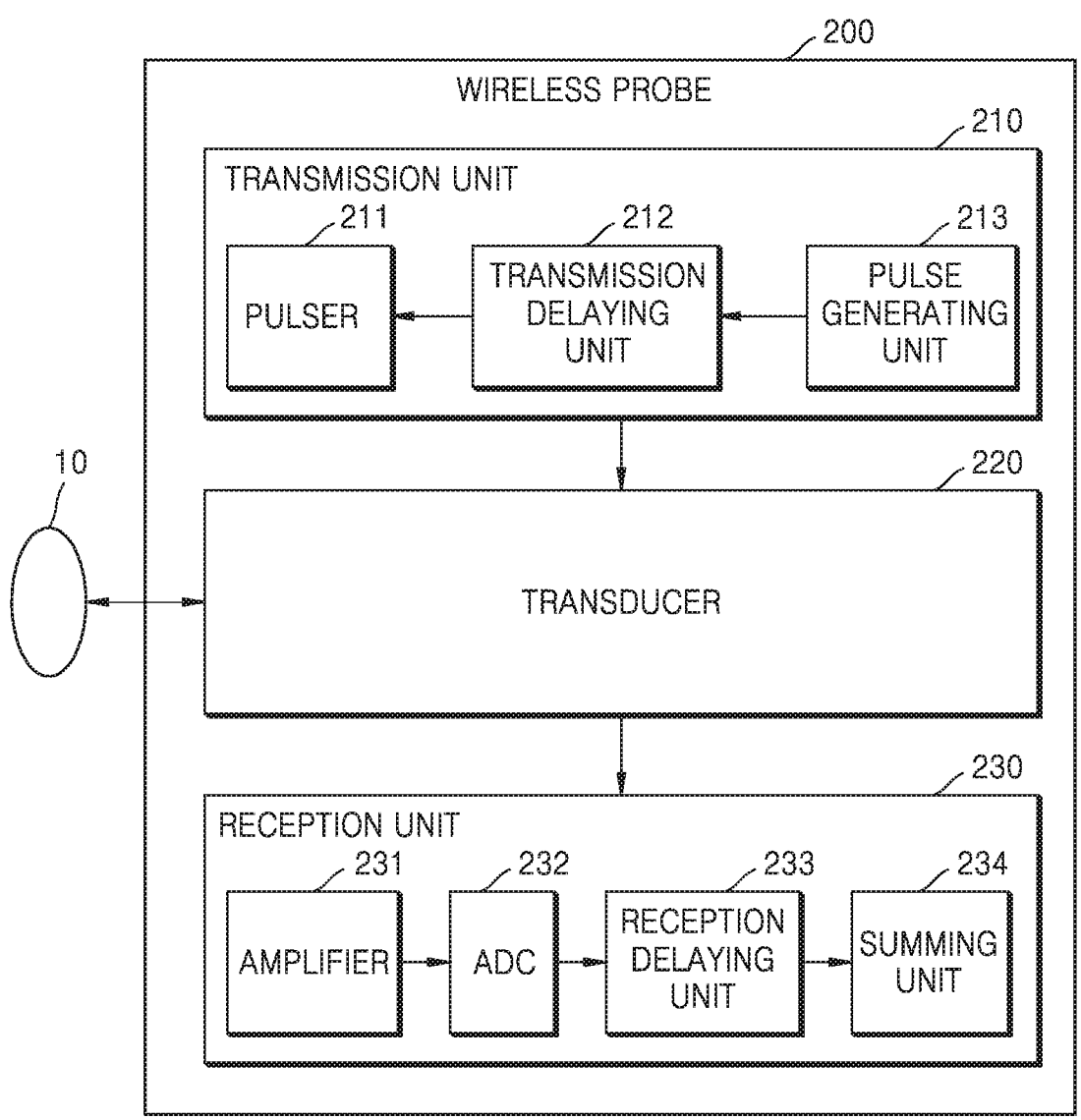
FIG. 2 is a block diagram illustrating a configuration of a wireless probe according to an exemplary embodiment.

FIG. 2 is a block diagram showing a configuration of a wireless probe 200 according to an embodiment. As described above with reference to FIG. 1, the wireless probe 200 may include a plurality of transducers, and, according to embodiments, may include some or all of the components of the ultrasound transceiver 110 shown in FIG. 1.

The wireless probe 200 according to the embodiment shown in FIG. 2 includes a transmitter 210, a transducer 220, and a receiver 230. Since descriptions thereof are given above with reference to FIG. 1, detailed descriptions thereof will be omitted here. In addition, according to embodiments, the wireless probe 200 may selectively include a reception delaying unit 233 and a summing unit 234.

The wireless probe 200 may transmit ultrasound signals to the object 10, receive echo signals from the object 10, generate ultrasound data, and wirelessly transmit the ultrasound data to the ultrasound diagnosis apparatus 100 shown in FIG. 1.

When a pregnant woman has an incompetent cervix or a cervix length (CL) of the pregnant woman is short, there is a risk of premature labor. Particularly, when a cervix length is equal to or less than 2.5 cm, a risk of premature labor is determined. However, it is difficult for an ultrasound diagnosis apparatus of the related art to measure a cervix length, which is an indicator of parturition or natural premature labor. For example, to perform an ultrasound diagnosis on a cervix, if certain pressure or more is not applied to the cervix, it is difficult to acquire an image capable of measuring the cervix. Also, if too high pressure is applied to the cervix, the cervix deforms, and for this reason, it is difficult to measure an accurate length. Therefore, a user applies appropriate pressure to the cervix depending on an experience of a doctor, and then, measures the cervix. Due to such problems, an inexperienced doctor has difficulties measuring the length of the cervix, and moreover, since pressures respectively applied to measured persons differ, a cervix length is often changed.

Therefore, it is required to develop an ultrasound diagnosis apparatus and a method of operating the same, which more accurately measure a cervix length.

Figure 3:
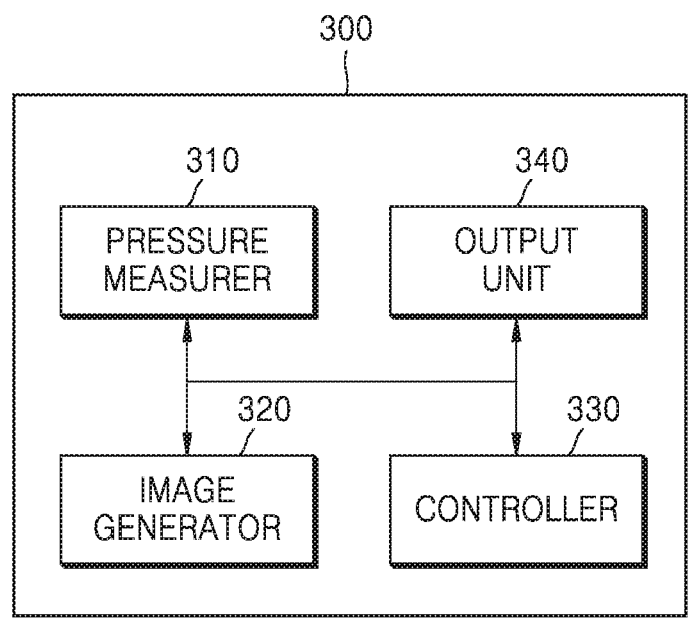
FIG. 3 is a block diagram of an ultrasound diagnosis apparatus according to an exemplary embodiment.

FIG. 3 is a block diagram of an ultrasound diagnosis apparatus 300 according to an exemplary embodiment.

Referring to FIG. 3, the ultrasound diagnosis apparatus 300 includes a pressure measurer 310, an image generator 320, a controller 330, and an output unit 340. At least one selected from the pressure measurer 310, the image generator 320, the controller 330, and the output unit 340 may be implemented with hardware. Also, the hardware may include a processor. The processor may be a general-use single-chip or multi-chip microprocessor (for example, an ARM processor), a special-purpose microprocessor (for example, a digital signal processor (DSP)), a microcontroller, or a programmable gate array. The processor may be referred to as a central processing unit (CPU). Some of the elements may use a combination of processors (for example, the ARM processor and the DSP).

The hardware may also include a memory. The memory may be an arbitrary electronic component capable of storing electronic information. The memory may be implemented with random access memory (RAM), read-only memory (ROM), a magnetic disk storage medium, an optical storage medium, a flash memory device of RAM, an on-board memory included in the processor, erasable programmable read-only memory (EPROM), electrically erasable and programmable read only memory (EEPROM), registers, or a combination thereof.

Data and commands may be stored in the memory. The commands may be executed by the processor so as to implement methods disclosed herein. Execution of the commands may include the use of data stored in the memory. When the processor executes the commands, various portions of the commands may be loaded into the processor, and various segments of data may be loaded into the processor.

The pressure measurer 310 measures a pressure value applied from a probe to a cervix. The image generator 320 scans an object to acquire an ultrasound image. Also, the controller 330 determines whether a cervix line is included in the ultrasound image. Also, when the cervix line is included in the ultrasound image, the controller 330 acquires the measured pressure value, corresponding to the ultrasound image, as a first pressure value. Also, the controller 330 acquires a second pressure value for measuring a length of the cervix line. Also, the output unit 340 outputs pressure information based on at least one selected from the first pressure value and the second pressure value.

The pressure measurer 310 may measure pressure applied from the probe to a cervix. The pressure measurer 310 may use a variant, a pressure sensor, and a transducer of the probe.

The image generator 320 corresponds to the image generator 122 of FIG. 1. The image generator 122 has been described above in detail, and thus, repeated descriptions of the image generator 320 are omitted.

When the cervix line is included in the ultrasound image, the controller 330 acquires the measured pressure value, corresponding to the ultrasound image, as the first pressure value. Also, the controller 330 acquires the second pressure value that is appropriate for measuring a length of the cervix line.

The controller 330 corresponds to the controller 170 of FIG. 1. The probe may acquire contour lines from a plurality of ultrasound images which are acquired by entering a cervix, and whether a cervix line is included in an ultrasound image may be determined by comparing the contour lines acquired from the plurality of ultrasound images.

The controller 330 may acquire, as the first pressure value, a pressure value corresponding to each of a plurality of ultrasound images after a time when a cervix line starts to appear. Also, the controller 330 may acquire, as pressure information, an arithmetic relationship between the first pressure value and the second pressure value. The output unit 340 may output, to a user, the pressure information based on at least one selected from the first pressure value and the second pressure value.

The pressure information is pressure information based on at least one selected from the first pressure value and the second pressure value. The pressure information may include at least one selected from the first pressure value and the second pressure value. Also, the pressure information may include information indicating the arithmetic relationship between the first pressure value and the second pressure value. The information indicating the arithmetic relationship is information which enables the user to easily know a relationship between the first pressure value and the second pressure value. For example, the information indicating the arithmetic relationship may include at least one selected from a ratio, a percentage, and a difference value between the first pressure value and the second pressure value.

The first pressure value may include a pressure value which is measured when a cervix line starts to appear in an ultrasound image. Also, the first pressure value may include a pressure value which is measured by the probe further applying pressure to a cervix after the cervix line appears in the ultrasound image.

The output unit 340 may output at least one of the first and second pressure values as at least one selected from a letter, a figure, a color, a sound, and vibration. The output unit 340 may include the display 140 of FIG. 1. Also, the output unit 340 may include a sound apparatus including at least one selected from a speaker, a headset, and an earphone. Also, the output unit 340 may include at least one selected from a bulb and a light-emitting diode (LED). Also, the output unit 340 may include a vibration element.

The second pressure value according to an exemplary embodiment may be a pressure value that is suitable for statistically measuring a cervix line. The memory 150 may store the second pressure value, which is acquired by a statistics method. The output unit 340 may output the second pressure value stored in the memory 150. The second pressure value may have one value. Also, the second pressure value may be a range of a pressure value that is suitable for measuring a cervix line.

Moreover, the second pressure value according to another exemplary embodiment may be a pressure value that is suitable for measuring a cervix line based on an experience of a user. The ultrasound diagnosis apparatus 300 may receive the second pressure value from the user. The second pressure value received from the user may be stored in the memory 150. The output unit 340 may output the second pressure value.

The user easily knows pressure suitable for measuring a cervix line, based on information provided by the ultrasound diagnosis apparatus 300.

Figure 4:
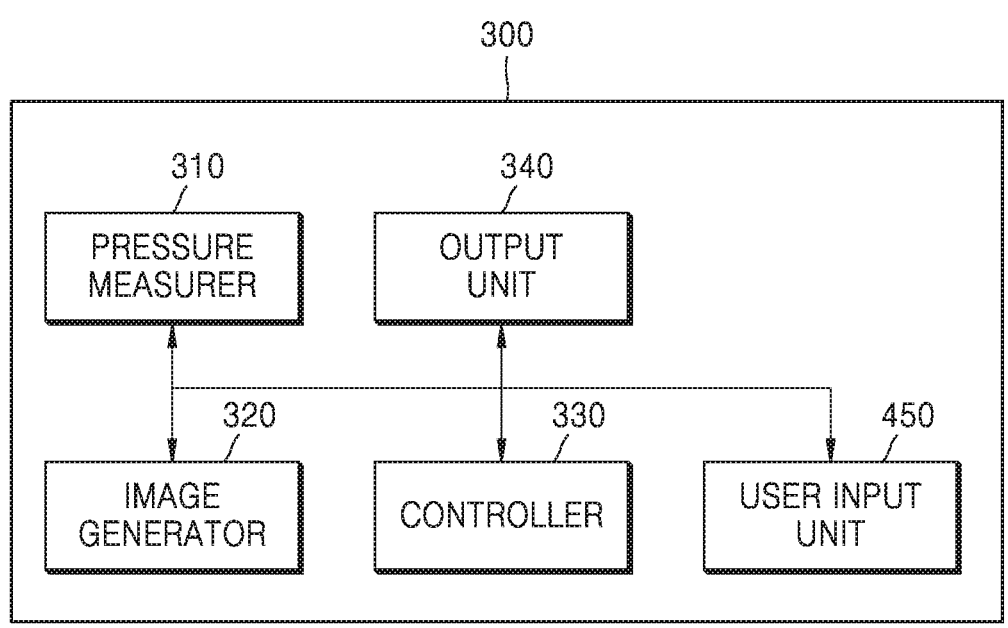
FIG. 4 is a block diagram of an ultrasound diagnosis apparatus according to an exemplary embodiment.

FIG. 4 is a block diagram of an ultrasound diagnosis apparatus 300 according to an exemplary embodiment.

Referring to FIG. 4, the ultrasound diagnosis apparatus 300 may include a pressure measurer 310, an image generator 320, a controller 330, an output unit 340, and a user input unit 450. The pressure measurer 310, the image generator 320, the controller 330, and the output unit 340 have been described above, and thus, their detailed descriptions are not provided. The user input unit 450 may receive a second pressure value from a user. The user input unit 450 may correspond to the input device 160 of FIG. 1.

Figure 5:
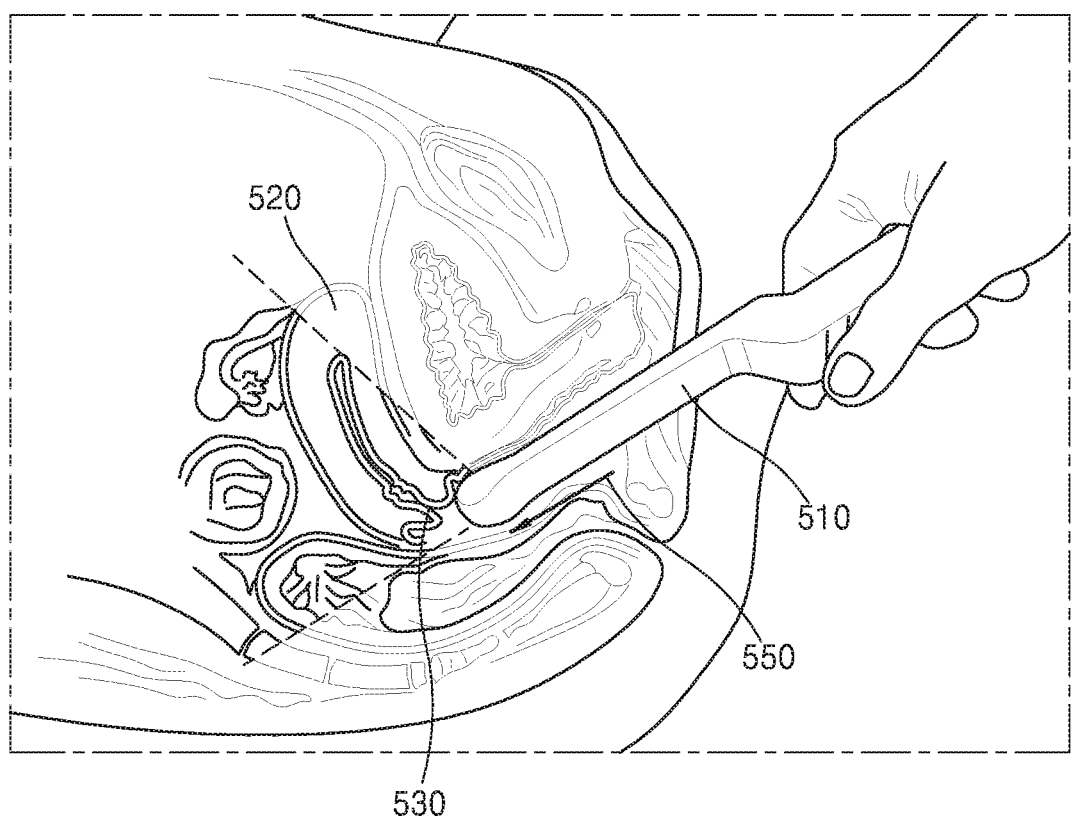
FIG. 5 is a diagram illustrating a process of measuring a cervix length, according to an exemplary embodiment.

FIG. 5 is a diagram illustrating a process of measuring a cervix length, according to an exemplary embodiment.

Referring to FIG. 5, a user may push a probe 510 into a body of an examinee toward a cervix line 530. The image generator 320 may acquire a plurality of ultrasound images, based on ultrasound data which is acquired from an object by the probe 510 entering the body of the examinee. When the probe 510 does not sufficiently deeply enter the body, a cervix line 530 may not appear in each of the plurality of ultrasound images. However, instead of the cervix line 530, an organ may appear in each of the plurality of ultrasound images. For example, a uterus 520 may appear in each of the plurality of ultrasound images. When the probe 510 sufficiently deeply enters the body, the cervix line 530 may not appear in each of the plurality of ultrasound images.

Moreover, although the probe 510 sufficiently deeply enters the body, if the probe 510 does not apply appropriate pressure to a cervix, the cervix line 530 may not appear in each of the plurality of ultrasound images.

Figure 6:
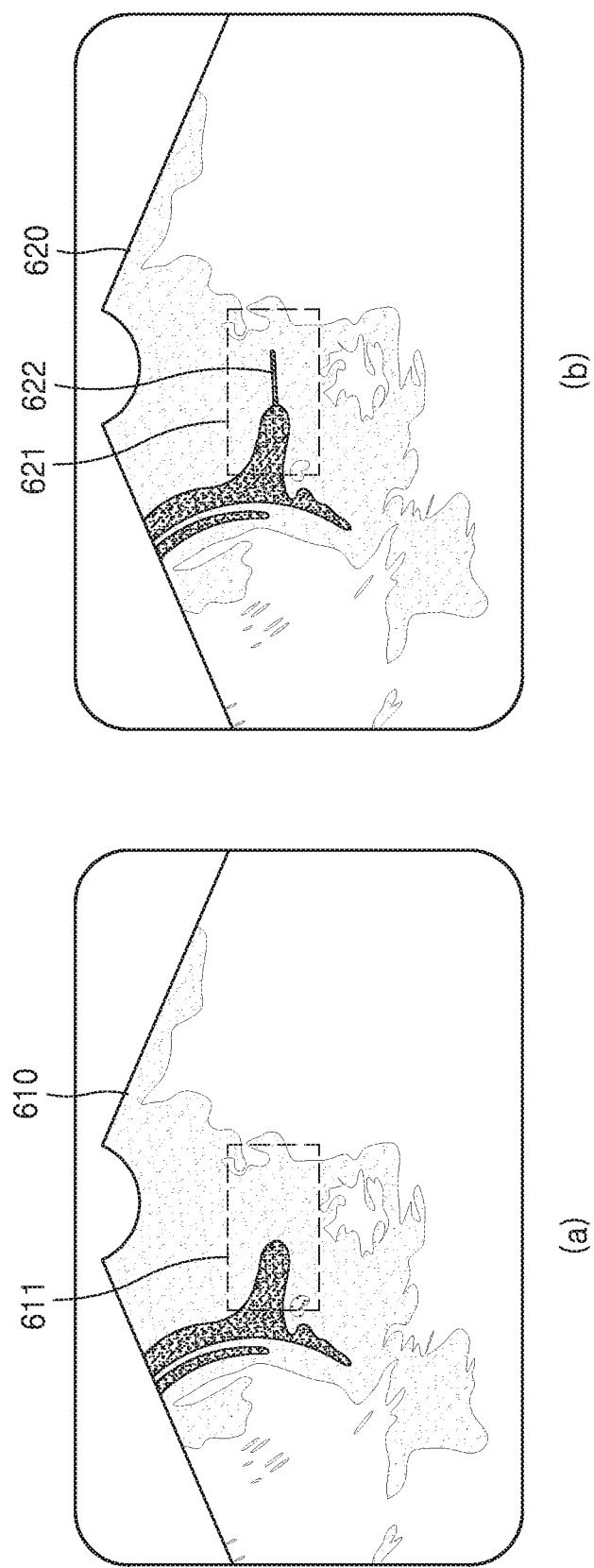
FIG. 6 is a diagram illustrating a plurality of ultrasound images according to an exemplary embodiment.

FIG. 6 is a diagram illustrating a plurality of ultrasound images according to an exemplary embodiment.

Referring to FIG. 6 (a), one 610 of a plurality of ultrasound images is illustrated. The ultrasound image 610 may represent a state in which a probe does not sufficiently deeply enter a body of an examinee. Alternatively, since the probe does not apply appropriate pressure to a cervix, the cervix line 530 may not appear in the ultrasound image 610.

Referring to a region 611 of the ultrasound image 610 of FIG. 6 (a), a cervix line does not normally appear. However, a head bone 612 of a fetus which is a larger object than the cervix line may appear in the ultrasound image 610. A user may adjust a position of the probe for finding the cervix line while looking at the ultrasound image 610. For example, by applying a force to the probe, the user may allow the probe to apply appropriate pressure to a cervix.

FIG. 6 (b) illustrates an ultrasound image 620 which appears when the probe applies appropriate pressure to the cervix. Referring to FIG. 6 (b), one 620 of a plurality of ultrasound images is illustrated. Referring to a region 621 of the ultrasound image 620, a cervix line 622 of an examinee is shown. The cervix line 622 of the ultrasound image 620 may be the cervix line 622 when the probe applies appropriate pressure to the cervix. However, when the probe applies pressure, which is equal to or higher than appropriate pressure, to the cervix, the cervix line 622 may be deformed, and for this reason, an error may occur in measuring a length of the cervix line 622.

When a cervix line is included in an ultrasound image, the controller 330 may acquire a measured pressure value, corresponding to the ultrasound image, as a first pressure value. The first pressure value may include a pressure value which is measured when the cervix line 622 starts to appear in the ultrasound image 620. Also, the first pressure value may include a pressure value which is measured by the probe further applying pressure to a cervix after the cervix line 622 appears in the ultrasound image 620.

The ultrasound diagnosis apparatus 300 may provide pressure that is appropriate for measuring a length of the cervix line 622. This will be described in detail with reference to FIGS. 8 to 10.

According to an exemplary embodiment, the user may manually acquire the ultrasound image 620, in which the cervix line 622 starts to appear, while looking at the ultrasound image 620.

Moreover, according to another exemplary embodiment, the ultrasound diagnosis apparatus 300 may automatically acquire whether there is the cervix line 622. For example, the image generator 320 may acquire a plurality of ultrasound images from different positions of the probe. Also, the controller 330 may compare the acquired plurality of ultrasound images to determine whether there is the cervix line 622.

In detail, the controller 330 may acquire, as a reference, a characteristic part from the plurality of ultrasound images. For example, the characteristic part may be a head bone 612 (613) of a fetus. The controller 330 may detect a vertical line having a deep arc shape to determine that the head bone 612 of the fetus appears in the ultrasound image 610. As a position of the probe changes, the plurality of ultrasound images acquired by the image generator 320 may gradually change. The controller 330 may compare the plurality of ultrasound images to detect the ultrasound image 620 in which a thin horizontal line, which does not appear in a previous ultrasound image 610, appears. The controller 330 may determine that the cervix line 622 is included in the ultrasound image 620 in which the thin horizontal line appears along with the head bone 623 of the fetus.

Figure 7:
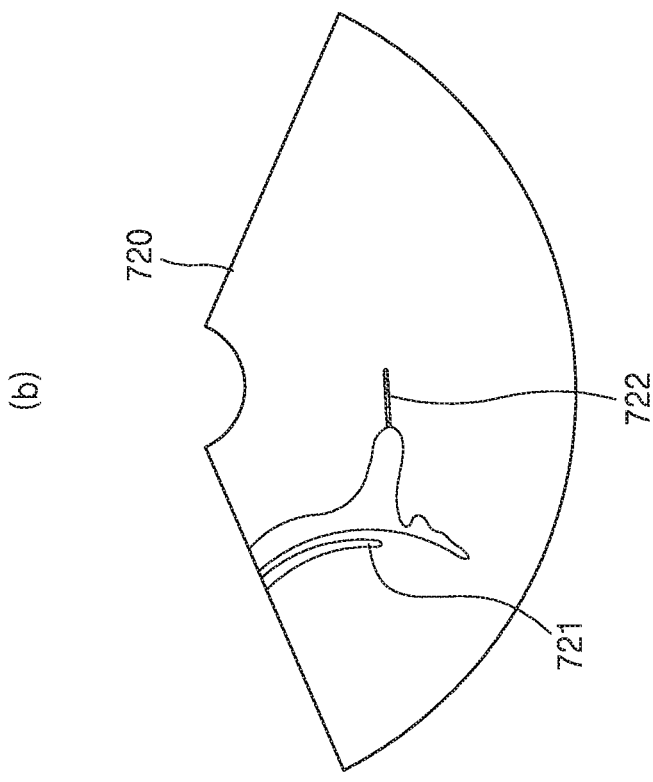
FIG. 7 is a diagram illustrating a plurality of ultrasound images according to an exemplary embodiment.
Figure 7:
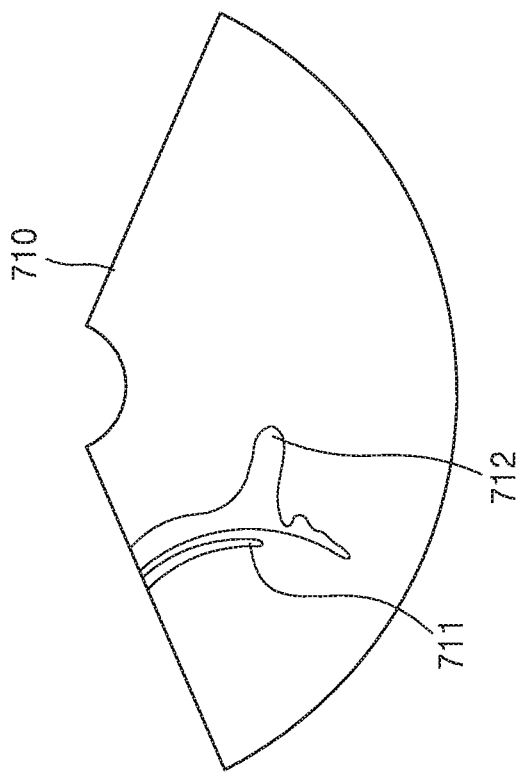

FIG. 7 is a diagram illustrating a plurality of ultrasound images according to an exemplary embodiment.

The controller 330 may detect a contour line from an ultrasound image by using at least one selected from a Sobel mask, a Prewitt mask, a Robert mask, and a Canny mask. Also, the controller 330 may determine whether there is a cervix line, based on the contour line.

For example, the controller 330 may detect the contour line by using the ultrasound image 610 of FIG. 6 (*a*). Referring to FIG. 7 (*a*), the ultrasound diagnosis apparatus 300 may acquire an ultrasound image 710 from which a contour line is detected. The detection of the contour line may be performed by at least one selected from the controller 330 of FIG. 3 and the image processor 120 of FIG. 1. At least one selected from the controller 330 and the image processor 120 may detect the contour line by using at least one selected from the Sobel mask, the Prewitt mask, the Robert mask, and the Canny mask.

The controller 330 may determine whether a contour line 711 of a head bone of a fetus is included in the ultrasound image 710 from which the contour line is detected. Also, the controller 330 may determine, as a reference ultrasound image 710, an ultrasound image after the contour line 711 of the head bone of the fetus appears.

When a probe enters a body of an examinee, the contour line 711 of the head bone of the fetus may appear before a cervix line appears. The cervix line does not appear in a contour line 712 of the reference ultrasound image 710. The controller 330 may detect a contour line from each of a plurality of ultrasound images which appear after the reference ultrasound image 710, and compare the contour line with the reference ultrasound image 710.

FIG. 7 (*b*) illustrates an ultrasound image 720 which appears when the probe applies pressure, which is suitable for observing a cervix of an examinee, to a cervix. For example, referring to FIG. 7 (*b*), the ultrasound diagnosis apparatus 300 may detect a contour line from the ultrasound image 620 of FIG. 6 (*b*). The ultrasound diagnosis apparatus 300 may detect the contour line to acquire the ultrasound image 720. The detection of the contour line may be performed by at least one selected from the controller 330 of FIG. 3 and the image processor 120 of FIG. 1.

The controller 330 may compare the reference ultrasound image 710 with the ultrasound image 720 to determine there is a cervix line 723. For example, the controller 330 may determine there is the cervix line 723, based on that a horizontal line, which is not included in the reference ultrasound image 710, appears in the ultrasound image 720.

Moreover, the controller 330 may determine whether there is a cervix line, based on a standard ultrasound image stored in the ultrasound diagnosis apparatus 300. For example, the ultrasound diagnosis apparatus 300 may store the standard ultrasound image including a cervix line. Also, the standard ultrasound image may be an ultrasound image when the probe applies pressure, which is suitable for observing a cervix line, to a cervix. The ultrasound diagnosis apparatus 300 may receive the standard ultrasound image from the user. Also, the ultrasound diagnosis apparatus 300 may store the standard ultrasound image in the memory 150 of FIG. 1.

The controller 330 may compare the standard ultrasound image with a plurality of ultrasound images to determine whether there is a cervix line. For example, a correlation between the ultrasound image 720 and the standard ultrasound image may be higher than a correlation between the ultrasound image 710 of FIG. 7 and the standard ultrasound image, and thus, the controller 330 may determine that the cervix line is included in the ultrasound image 720. Also, a correlation between the ultrasound image 720 and the standard ultrasound image may be higher than a correlation between the ultrasound image 610 of FIG. 6 and the standard ultrasound image, and thus, the controller 330 may determine that the cervix line is included in the ultrasound image 620.

Moreover, the controller 330 may compare a plurality of ultrasound images to determine whether there is a cervix line, based on whether a horizontal line appears.

When a cervix line is included in an ultrasound image, the controller 330 may acquire a measured pressure value, corresponding to the ultrasound image, as a first pressure value. The first pressure value may include a pressure value which is measured when a cervix line 722 starts to appear in the ultrasound image 720. Also, the first pressure value may include a pressure value which is measured by the probe further applying pressure to a cervix after the cervix line 722 appears in the ultrasound image 720.

FIGS. 8A to 8D are diagrams illustrating a probe 800 according to an exemplary embodiment.

Figure 8A:
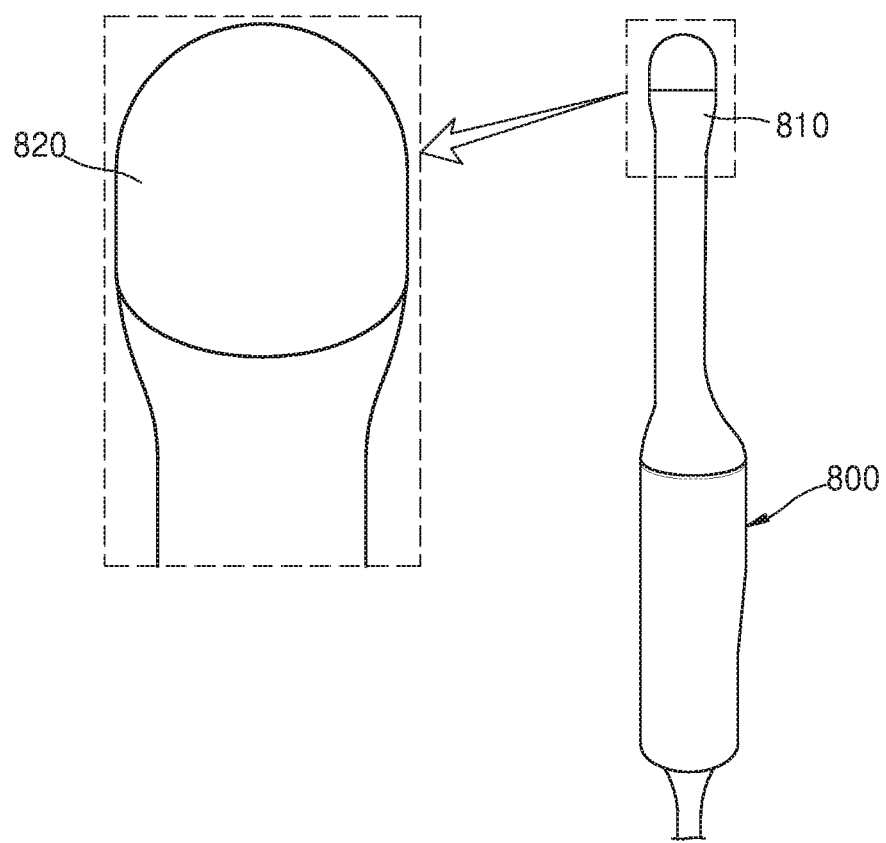
FIGS. 8A to 8D are diagrams illustrating a probe according to an exemplary embodiment.

Referring to FIG. 8A, an upper part 810 of the probe 800 may be enlarged and referred to by reference numeral 820. The upper part 810 of the probe 800 may apply pressure to an object. Therefore, the pressure measurer 310 for measuring pressure may be included in the upper part 810 of the probe 800. The probe 800 may correspond to at least one selected from the probe 20 of FIG. 1 and the wireless probe 200 of FIG. 2.

Figure 8B:
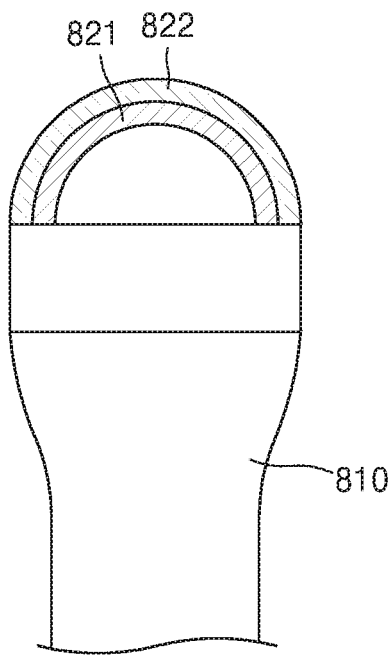

Referring to FIG. 8B, the pressure measurer 310 may include a variant 822, which is disposed in front of a transducer 821 of the probe 800. Also, the pressure measurer 310 may measure a pressure value, based on a deformation degree of the variant 822, which appears in an ultrasound image, and an elastic coefficient of the variant 822.

The variant 822 includes a material which has a certain thickness, low-attenuation sound characteristics, a damping value, and an elastic value. The variant 822 may be disposed at one side of the ultrasound probe 800 and may be deformed according to pressure which is applied through the ultrasound probe 800. The variant 822 may include a solid gel, silicon, and a fluid pocket. Referring to FIG. 8B, the variant 822 may be disposed on the transducer 821 of the probe 800 (for example, a linear probe, a phase array probe, a convex probe, or a three-dimensional (3D) probe, and may contact a surface of the object.

Figure 8C:
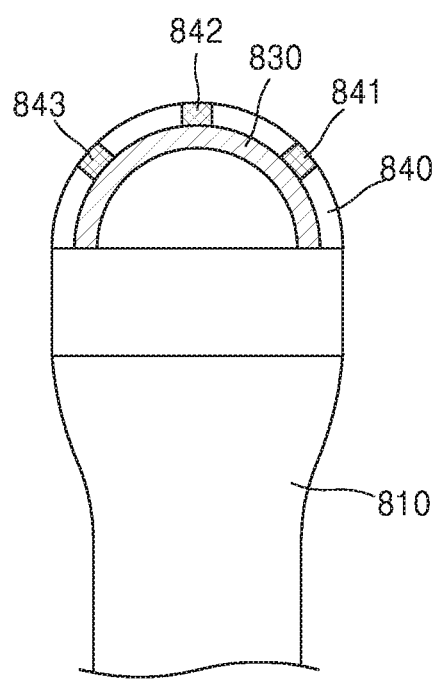

Referring to FIG. 8C, the pressure measurer 310 may include a pressure sensor 840, which is disposed in the probe 800. Also, the pressure measurer 310 may measure a pressure value, based on an output of the pressure sensor 840. Referring to FIG. 8C, the pressure sensor 840 may be disposed on the transducer 830. The pressure sensor 840 may include a plurality of pressure sensors 841 to 843.

When pressure is applied to the pressure sensors 841 to 843, each of the pressure sensors 841 to 843 may output a pressure value as at least one selected from a digital value and an analog value. Therefore, the ultrasound diagnosis apparatus 300 may acquire the pressure value, based on an output of each of the pressure sensors 841 to 843.

Figure 8D:
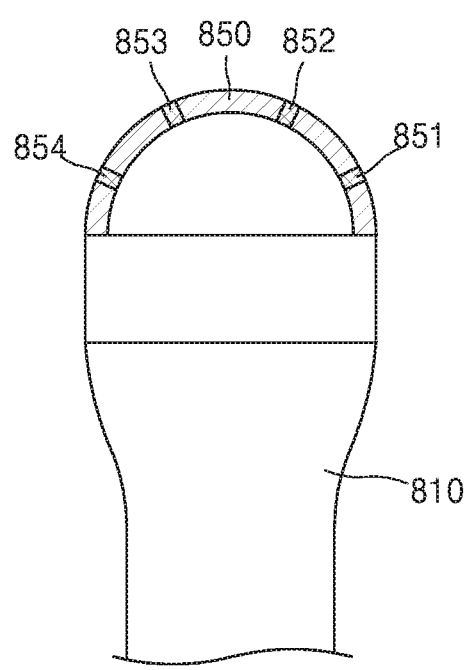

Referring to FIG. 8D, the pressure measurer 310 may include a plurality of piezo elements 851 to 854. When each of the piezo elements 851 to 854 is deformed by pressure applied thereto, each of the piezo elements 851 to 854 generates a voltage. The pressure measurer 310 may include an array 850 of the piezo elements 851 to 854. Also, when a voltage is applied to each of the piezo elements 851 to 854, each of the piezo elements 851 to 854 deforms.

The pressure measurer 310 may measure a pressure value, based on an electrical signal output from each of the piezo elements 851 to 854. Also, each of the piezo elements 851 to 854 may be at least one of a plurality of transducers included in the probe 800. That is, the transducers included in the probe 800 may be configured with a plurality of piezo elements, and each of the piezo elements 851 to 854 may be at least one of the piezo elements configuring the transducers. Also, the piezo elements 851 to 854 may be piezo elements which are equipped in the probe 800 separately from the transducers, for measuring pressure.

The piezo elements 851 to 854 are elements which each output an electrical signal when pressure is applied thereto. Therefore, the ultrasound diagnosis apparatus 300 may acquire a pressure value, based on the electrical signal output from each of the piezo elements 851 to 854.

Figure 9:
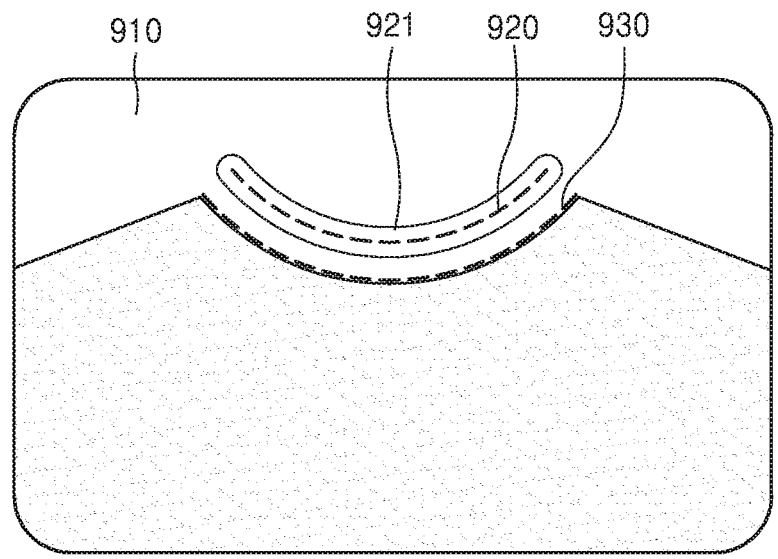
FIG. 9 is a diagram illustrating an ultrasound image for measuring a pressure value by using a variant, according to an exemplary embodiment.

FIG. 9 is a diagram illustrating an ultrasound image for measuring a pressure value by using a variant, according to an exemplary embodiment.

Referring to FIGS. 8A and 9, the image generator 320 may acquire an ultrasound image 910. Since the variant 822 is disposed on the transducer 821, a boundary image 921 of the variant 822 and the transducer 821 may appear in the ultrasound image 910. Also, the ultrasound diagnosis apparatus 300 may perform image processing on the boundary image 921 to acquire a center line 920. Also, the ultrasound diagnosis apparatus 300 may perform image processing on the ultrasound image 910 to acquire a boundary line 930 of the variant 822 and an object. The ultrasound diagnosis apparatus 300 may acquire a gap between the center line 920 and the boundary line 930 as a thickness of the variant 822.

The pressure measurer 310 may measure a pressure value, based on a deformation degree of the variant 822 and an elastic coefficient of the variant 822. A force applied from the variant 822 to an object may be calculated as expressed in the following Equation (1):

$$F = kx + cx' \quad (1)$$

where F denotes a force applied from the variant 822 to the object, k denotes the elastic coefficient of the variant 822, x denotes a deformation amount (a length) of the variant 822, c denotes a damping coefficient of the variant 822, and x' denotes the deformation amount of the variant 822.

Pressure may be calculated as expressed in the following Equation (2):

$$P = F/S \quad (2)$$

where P is pressure, F is a force applied from the variant 822 to the object, and S is a width of a surface of the variant 822.

That is, the pressure measurer 310 may acquire the thickness of the variant 822 as the gap between the center line 920 and the boundary line 930, based on the ultrasound image 910. Also, the pressure measurer 310 may calculate a deformation amount "x" of the thickness of the variant 822 caused by the force "F" applied to the variant 822. Also, the variant 822 may have a certain elastic coefficient and a certain damping coefficient. Therefore, the pressure measurer 310 may calculate the force "F" applied to the variant 822, based on the ultrasound image 910. Also, the width of the surface of the variant 822 is almost constant, and thus, pressure applied to the variant 822 is calculated.

Figure 10A:
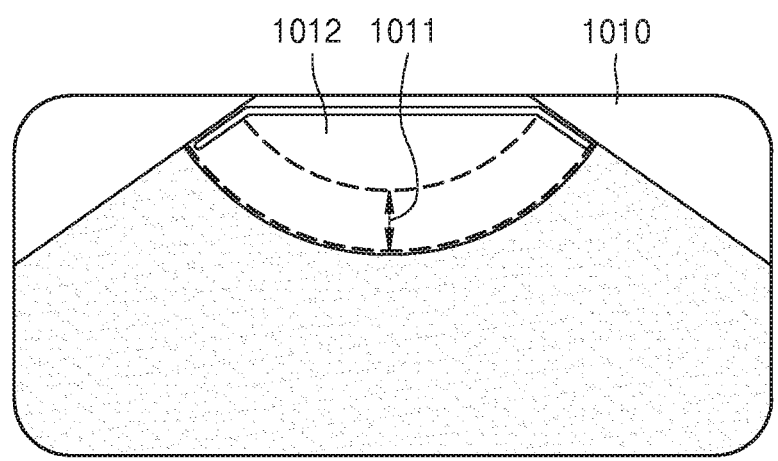
FIGS. 10A to 10C are diagrams illustrating ultrasound images according to an exemplary embodiment.
Figure 10B:
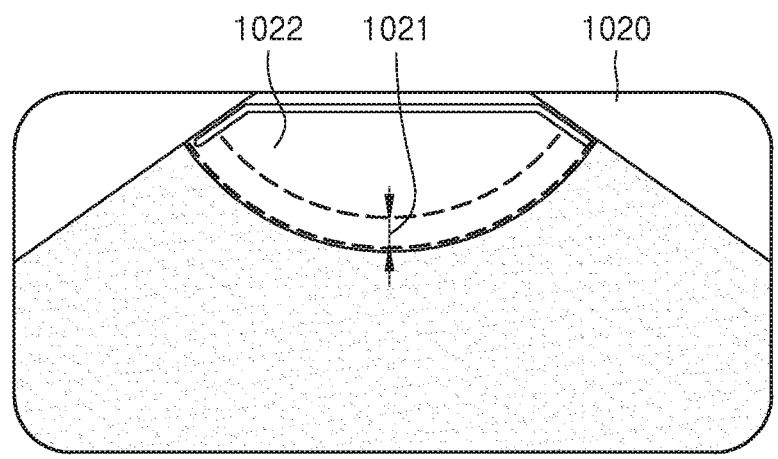
Figure 10C:
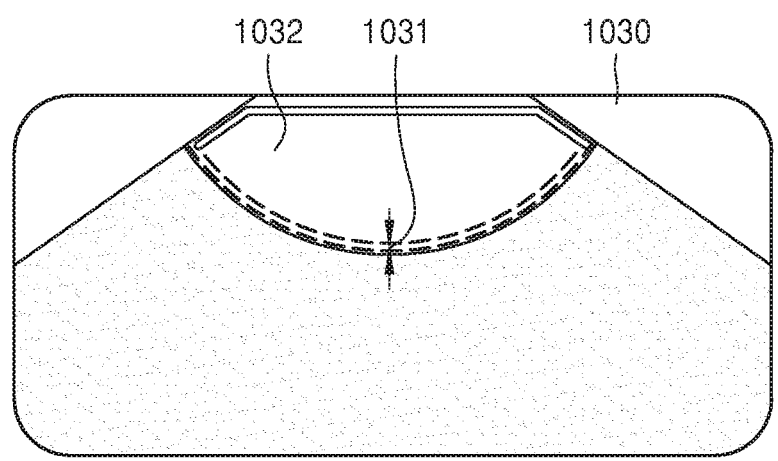

FIGS. 10A to 10C are diagrams illustrating ultrasound images according to an exemplary embodiment.

Referring to FIGS. 10A to 10C, the output unit 340 may output pressure information based on at least one selected from a first pressure value and a second pressure value. Also, the output unit 340 may output the pressure information as at least one selected from a letter, a figure, a color, a sound, and vibration.

When a cervix line is included in an ultrasound image, the controller 330 may acquire a measured pressure value, corresponding to the ultrasound image, as a first pressure value. The first pressure value may include a pressure value which is measured when the cervix line starts to appear in the ultrasound image 620. Also, the first pressure value may include a pressure value which is measured by the probe further applying pressure to a cervix after the cervix line appears in the ultrasound image 620.

Moreover, the second pressure value according to an exemplary embodiment may be a pressure value that is suitable for statistically measuring a cervix line. The memory 150 of FIG. 1 may store the second pressure value, which is acquired by a statistics method. The output unit 340 may output the second pressure value stored in the memory 150.

Moreover, the second pressure value according to another exemplary embodiment may be a pressure value that is suitable for measuring a cervix line based on an experience of a user. The ultrasound diagnosis apparatus 300 may receive the second pressure value from the user. The second pressure value received from the user may be stored in the memory 150. The output unit 340 may output the second pressure value.

Hereinafter, FIGS. 10A to 10C will be described along with FIG. 8. Referring to FIGS. 10A to 10C, it may be seen that thicknesses of the variant 822 differ. It may be seen that a thickness 1011 of the variant 822 in FIG. 10A is longest, a thickness 1021 of the variant 822 in FIG. 10B is the second longest, and a thickness 1031 of the variant 822 in FIG. 10C is shortest. That is, the ultrasound image 1010 is an image in which the probe applies lowest pressure to the object, and the ultrasound image 1030 is an image in which the probe applies a highest pressure to the object.

For example, in the ultrasound image 1020, a pressure value corresponding to the thickness 1021 of the variant 822 may be the second pressure value that is optimal for measuring a cervix line. The output unit 340 may include a display, which may display the ultrasound image 1020. Also, the ultrasound diagnosis apparatus 300 may compare a thickness, corresponding to the second pressure value, with thicknesses 1011, 1021 and 1031. The ultrasound diagnosis apparatus 300 may determine the thicknesses 1011 and 1031 as thicknesses corresponding to an inappropriate pressure value. Also, the ultrasound diagnosis apparatus 300 may add a comparison result to pressure information. The ultrasound diagnosis apparatus 300 may output the pressure information as at least one selected from a letter, a figure, a color, a sound, and vibration.

For example, the display may display one region 1022 of the ultrasound image 1020 unlike regions 1012 and 1032 of the ultrasound images 1010 and 1030. For example, the region 1022 may have a color which differs from those of the regions 1012 and 1032. Also, the display may display at least one selected from a letter and a figure in the one region 1022 of the ultrasound image 1020. Also, the display may display a figure, which is used for induction in order for the thicknesses 1011 and 1031 of the variant 822 to become the thickness 1021, in the regions 1012 and 1032 of the ultrasound images 1010 and 1030.

Moreover, the output unit 340 may include a sound apparatus, which may output a certain sound when the ultrasound image 1020 is displayed. Also, the sound apparatus may output a sound when the ultrasound images 1010 and 1030 are displayed, and then, when the ultrasound image 1020 is displayed, the sound apparatus may not output the sound. Also, the output unit 340 may include a vibration apparatus, which may output certain vibration when the ultrasound image 1020 is displayed. Also, the vibration apparatus may output vibration when the ultrasound images 1010 and 1030 are displayed, and then, when the ultrasound image 1020 is displayed, the sound apparatus may not output the vibration.

Figure 11:
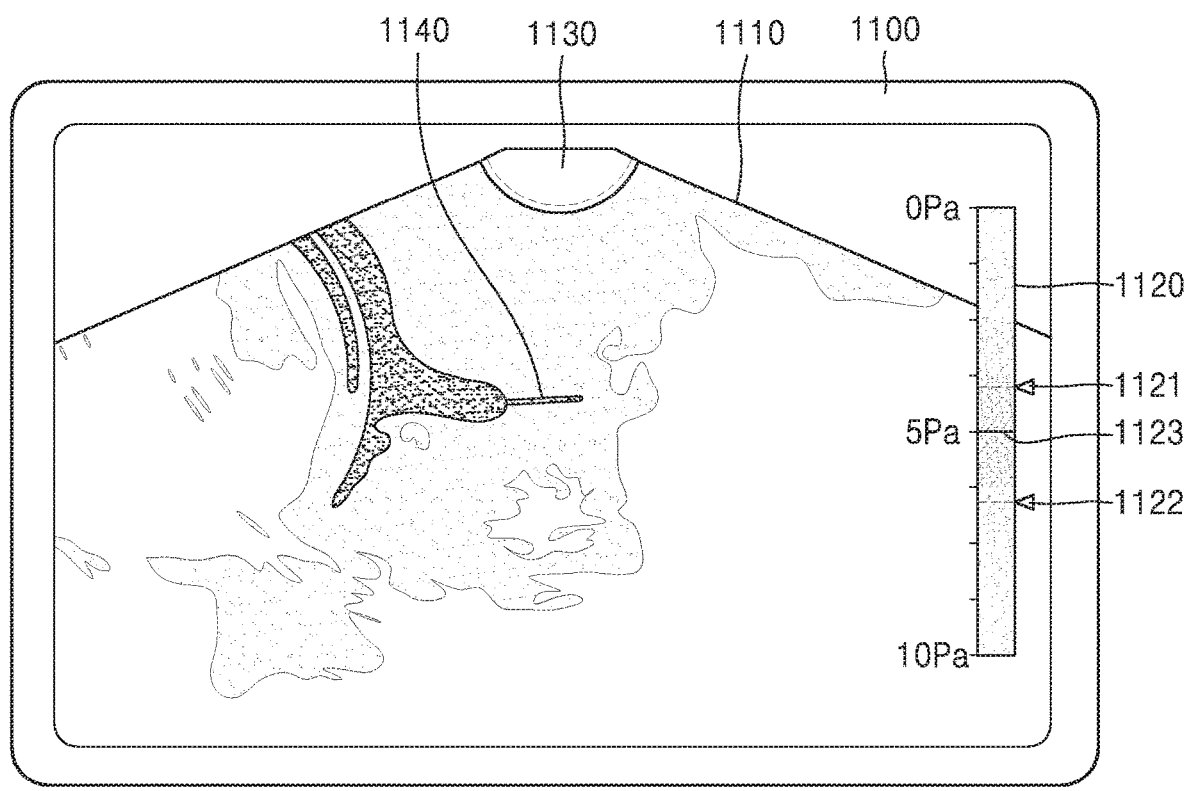
FIG. 11 is a diagram illustrating an ultrasound image according to an exemplary embodiment.

FIG. 11 is a diagram illustrating an ultrasound image 1110 according to an exemplary embodiment.

Referring to FIG. 11, a display 1100 may display the ultrasound image 1110. Also, the display 1100 may display a bar-shaped pressure indication region 1120. The display 1100 may mark a pressure value (for example, 0 Pa to 10 Pa) on the pressure indication region 1120. Also, the display 1100 may display the pressure indication region 1120 (for example, 0 Pa to 10 Pa) in different colors.

According to an exemplary embodiment, the second pressure value may have a range and include a minimum second pressure value and a maximum second pressure value. Also, a value between the minimum second pressure value and the maximum second pressure value may be a value suitable for measuring a cervix line. The display 1100 may display a minimum second pressure value indicator 1122 and a maximum second pressure value indicator 1121. The ultrasound diagnosis apparatus 300 may add the second pressure value to pressure information. A user may adjust pressure, which is applied from the probe to a cervix, while looking at the minimum and maximum second pressure value indicators 1122 and 1121.

According to an exemplary embodiment, the display 1100 may display an indicator 1123 that indicates the pressure applied from the probe to the cervix. A pressure value applied from the probe to the cervix may be the first pressure value.

The ultrasound diagnosis apparatus 300 may determine whether the first pressure value is included in a range of the second pressure value. In the ultrasound diagnosis apparatus 300, when the first pressure value is included in the range of the second pressure value, the indicator 1123 may be disposed between the maximum second pressure value indicator 1121 and the minimum second pressure value indicator 1122 as displayed in the display 1100. Also, the ultrasound diagnosis apparatus 300 may add a comparison result to the pressure information. The output unit 340 may output the pressure information as at least one selected from a letter, a figure, a color, a sound, and vibration.

For example, when the first pressure value is included in the range of the second pressure value, the display 1100 may display a region 1130 in a certain color. The certain color may be a color corresponding to a position in which the indicator 1123 is positioned in the pressure indication region 1120. The user easily checks pressure optimal for measuring a cervix line while looking at a color of the region 1130. The user may measure a length of a cervix line 1140 while checking a pressure value applied by the ultrasound diagnosis apparatus 300. Also, the ultrasound diagnosis apparatus 300 may perform image processing on the ultrasound image 1110 to automatically measure the length of the cervix line 1140. For example, as illustrated in FIG. 7 (*b*), the ultrasound diagnosis apparatus 300 may measure a length of a horizontal line which is generated through image processing.

Figure 12:
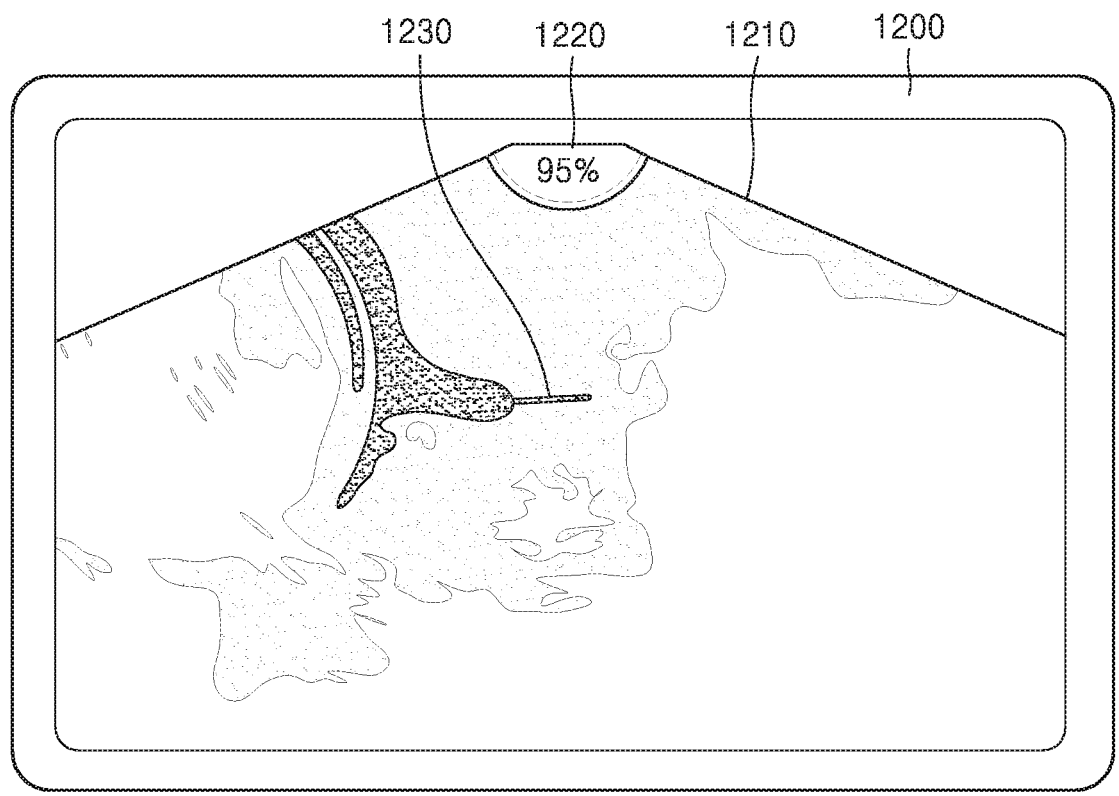
FIG. 12 is a diagram illustrating an ultrasound image according to an exemplary embodiment.

FIG. 12 is a diagram illustrating an ultrasound image according to an exemplary embodiment.

The output unit 340 may display an ultrasound image 1210. The output unit 340 may display pressure information. For example, the pressure information may include information indicating an arithmetic relationship between a first pressure value and a second pressure value. The second pressure value may be a pressure value that is suitable for measuring a cervix line. The ultrasound diagnosis apparatus 300 may calculate a percentage of the first pressure value to the second pressure value as the arithmetic relationship between the first pressure value and the second pressure value. For example, the controller 330 may calculate a percentage as expressed in the following Equation (3):

$$\text{percentage (\%)} = (\text{first pressure value})/(\text{second pressure value}) \times 100 \qquad (3)$$

The output unit 340 may display a value of a percentage, included in the pressure information, in a certain region 1220. A user may measure a length of a cervix line 1230 from an appropriate level of percentage while checking a percentage. Also, the ultrasound diagnosis apparatus 300 may perform image processing on the ultrasound image 1210 to automatically measure the length of the cervix line 1230.

The output unit 340 may output the pressure information as at least one selected from a letter, a figure, a color, a sound, and vibration. This has been described above with reference to FIGS. 10 and 11, and thus, the same descriptions are not repeated.

Figure 13:
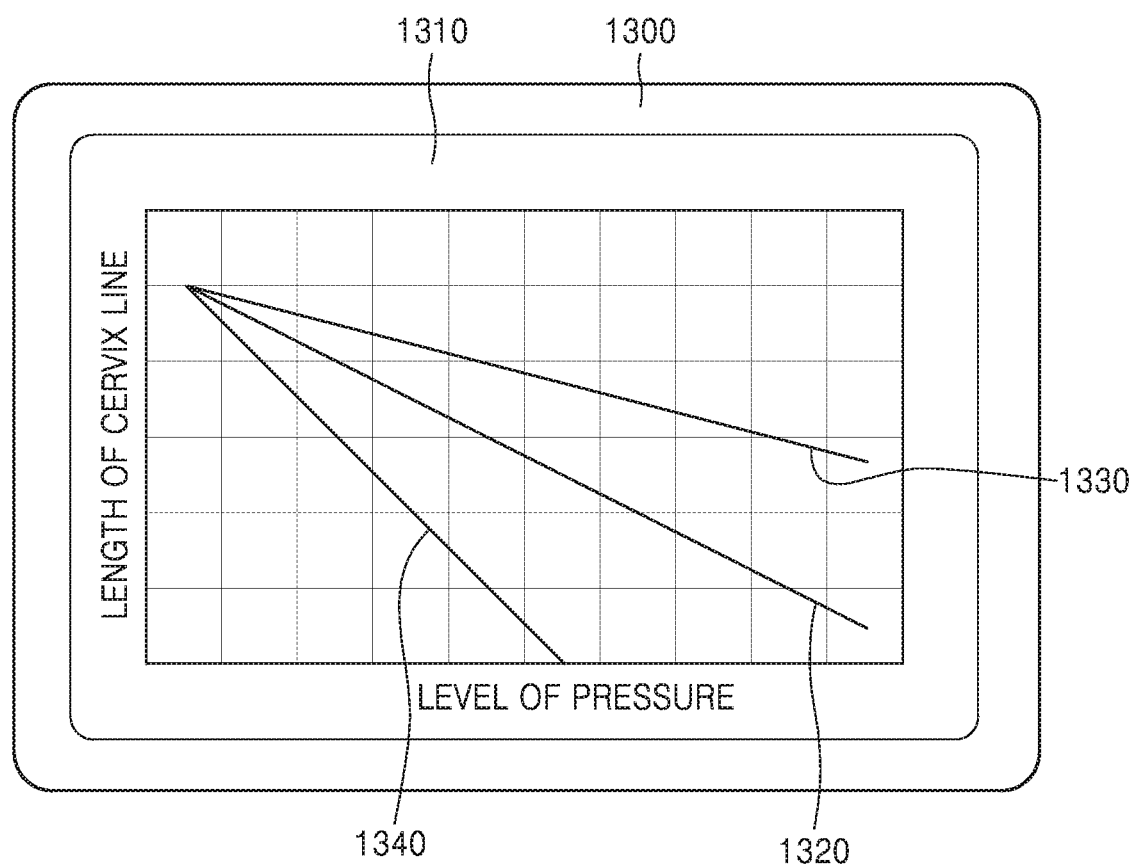
FIG. 13 is a diagram showing a graph according to an exemplary embodiment.

FIG. 13 is a diagram showing a graph according to an exemplary embodiment.

The pressure measurer 310 may measure a pressure value applied from the probe to a cervix. Also, a data acquirer may scan an object to acquire ultrasound data. Also, the controller 330 may measure a length of a cervix line from the ultrasound data. Also, the controller 330 may perform control to display a relationship between a change amount of the measured pressure value and a change amount of the length of the cervix line corresponding to the measured pressure value.

The data acquirer acquires the ultrasound data about the object. Also, the data acquirer may acquire the ultrasound data by using the ultrasound transceiver 110 of FIG. 1. Also, the data acquirer may acquire the ultrasound data from at least one selected from the server 32, the medical apparatus 34, and the portable terminal 36 over the network 30 of FIG. 1.

Referring to FIG. 13, the output unit 340 may include a display 1300. The display 1300 may display a graph 1310. The display 1300 may display a change in a length of a cervix line which is caused by a change in pressure applied from the probe to a cervix. Also, the display 1300 may display a standard line 1320. The standard line 1320 may be obtained statistically or based on an experience of a user. The standard line 1320 may be a change in a length of a cervix line which is caused by a change in pressure applied to a cervix of a normal examinee. Also, the standard line 1320 may be a reference of the change in the length of the cervix line which is caused by the change in the pressure applied to the cervix.

As described above with reference to FIGS. 5 to 12, the ultrasound diagnosis apparatus 300 may measure pressure applied to a cervix and a length of a cervix line. Also, the display 1300 may display, as a line 1330, a change in the length of the cervix line which is caused by a change in the pressure applied to the cervix. The user may check the standard line 1320 and the line 1330, which are displayed by the display 1300, and make a diagnosis. For example, a slope of the line 1330 is gentler than that of the standard line 1320. Therefore, it may be seen that a cervix is stiffer than a standard.

Moreover, for example, the display 1300 may display, as a line 1340, a change in the length of the cervix line which is caused by a change in the pressure applied to the cervix. The user may check the standard line 1320 and the line 1340, which are displayed by the display 1300, and make a diagnosis. For example, a slope of the line 1340 is steeper than that of the standard line 1320. Therefore, it may be seen that the cervix is softer than the standard. The user easily determines an incompetent cervix of an examinee, based on a graph 1310. Also, the user easily determines a possibility of premature labor, based on the graph 1310.

Figure 14:
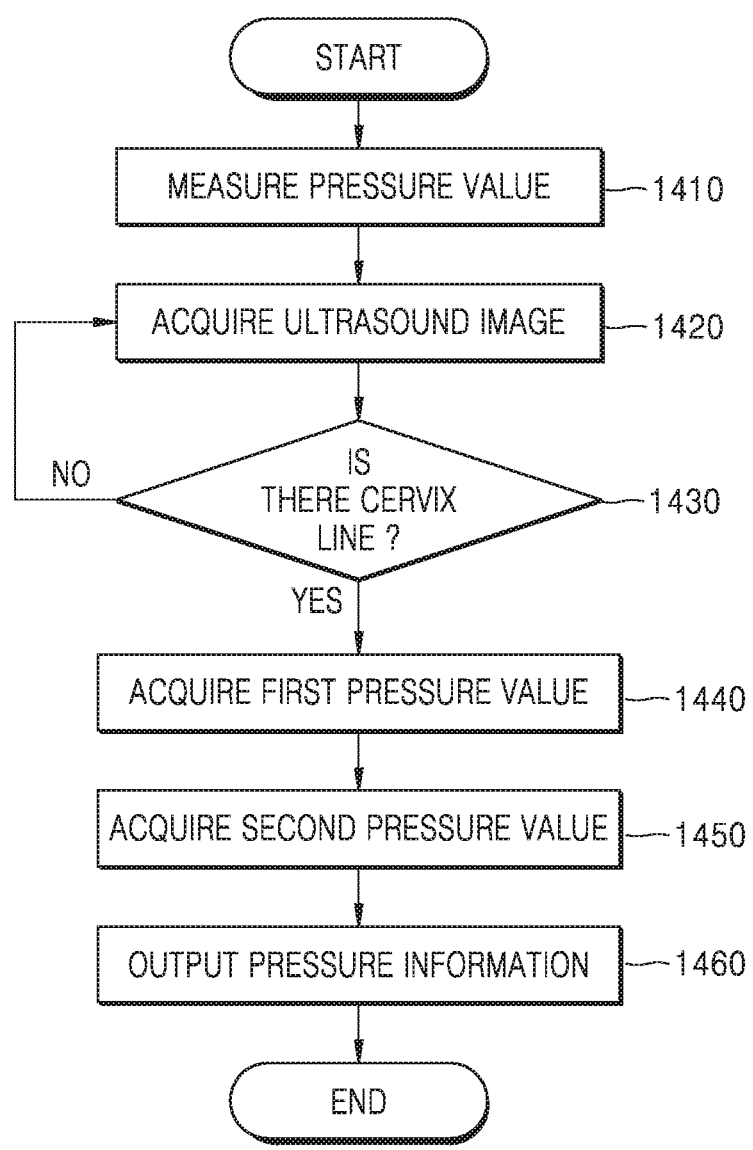
FIG. 14 is a flowchart illustrating a method of operating an ultrasound diagnosis apparatus, according to an exemplary embodiment.

FIG. 14 is a flowchart illustrating a method of operating an ultrasound diagnosis apparatus, according to an exemplary embodiment.

The ultrasound diagnosis apparatus has been described above with reference to FIGS. 3 and 4, and thus, the same descriptions are not repeated. Referring to FIG. 14, the method of operating the ultrasound diagnosis apparatus may include: operation 1410 of measuring a pressure value applied from the probe to a cervix; operation 1420 of scanning an object to acquire an ultrasound image; operation 1430 of determining whether a cervix line is included in the ultrasound image; operation 1440 of acquiring the measured pressure value, corresponding to the ultrasound image, as a first pressure value when the cervix line is included in the ultrasound image; operation 1450 of acquiring a second pressure value for measuring a length of the cervix line; and operation 1460 of outputting pressure information based on at least one selected from the first pressure value and the second pressure value.

In operation 1410, the pressure measurer 310 may measure a pressure value applied from the probe to a cervix. In operation 1420, the image generator 320 may scan an object to acquire an ultrasound image. In operation 1430, the controller 330 may determine whether a cervix line is included in the ultrasound image. In operation 1440, if the cervix line is included in the ultrasound image, the controller 330 may acquire the measured pressure value, corresponding to the ultrasound image, as a first pressure value. Also, if the cervix line is not included in the ultrasound image, the controller 330 may allow the image generator 320 to acquire the ultrasound image in operation 1420. In operation 1450, the controller 330 may acquire a second pressure value, which is a value suitable for measuring a length of the cervix line. In operation 1460, the output unit 340 may output at least one selected from the first pressure value and the second pressure value.

Moreover, operation 1420 of acquiring the ultrasound image may include an operation of acquiring a plurality of ultrasound images from different positions of the probe. Also, operation 1430 of determining whether the cervix line is included in the ultrasound image may include an operation of comparing the acquired plurality of ultrasound images to determine whether there is the cervix line.

Moreover, operation 1430 of determining whether the cervix line is included in the ultrasound image may include an operation of detecting a contour line from the ultrasound image by using at least one selected from the Sobel mask, the Prewitt mask, the Robert mask, and the Canny mask. Also, operation 1430 of determining whether the cervix line is included in the ultrasound image may include an operation of determining whether there is the cervix line, based on the contour line.

Moreover, the method of operating the ultrasound diagnosis apparatus may further include an operation of acquiring, as pressure information, an arithmetic relationship between the first pressure value and the second pressure value.

Moreover, operation 1460 of outputting the pressure information may include an operation of outputting the pressure information as at least one selected from a letter, a figure, a color, a sound, and vibration.

Moreover, the method of operating the ultrasound diagnosis apparatus may further include an operation in which the user input unit 450 receives the second pressure value from the user.

Moreover, a variant is disposed in front of a transducer of the probe. Operation 1410 of measuring the pressure value may include an operation of measuring a pressure value, based on a deformation degree of the variant which appears in the ultrasound image and an elastic coefficient of the variant.

Moreover, the probe may include a pressure sensor. Operation 1410 of measuring the pressure value may include an operation of measuring the pressure value, based on an output of the pressure sensor.

Moreover, the probe may include a piezo element. Operation 1410 of measuring the pressure value may include an operation of measuring the pressure value, based on an electrical signal output from the piezo element.

Figure 15:
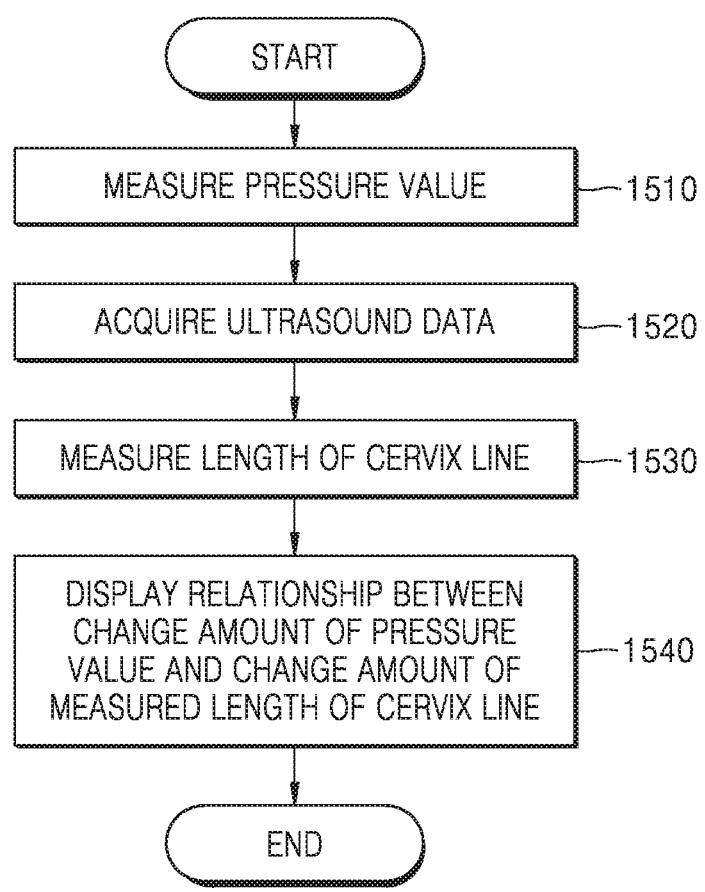
FIG. 15 is a flowchart illustrating a method of operating an ultrasound diagnosis apparatus, according to another exemplary embodiment.

FIG. 15 is a flowchart illustrating a method of operating an ultrasound diagnosis apparatus, according to another exemplary embodiment.

Referring to FIG. 15, the method of operating the ultrasound diagnosis apparatus may include: operation 1510 of measuring a pressure value applied from the probe to a cervix; operation 1520 of scanning an object to acquire ultrasound data; operation 1530 of measuring a length of a cervix line from the ultrasound data; and operation 1540 of displaying a relationship between a change amount of the measured pressure value and a change amount of the length of the cervix line corresponding to the measured pressure value.

In operation 1510, the pressure measurer 310 may measure a pressure value applied from the probe to a cervix. In operation 1520, the data acquirer may scan an object to acquire ultrasound data. In operation 1530, the controller 330 may measure a length of a cervix line from the ultrasound data. In operation 1540, the controller 330 may allow the output unit 340 to display a relationship between a change amount of the measured pressure value and a change amount of the length of the cervix line corresponding to the measured pressure value.

As described above, according to the one or more of the above exemplary embodiments, since the ultrasound diagnosis apparatus 300 provides a pressure value which enables a cervix line to be accurately measured, even an unskilled user measures the cervix line easily and accurately. Also, since the ultrasound diagnosis apparatus 300 provides a relationship between a cervix line and pressure applied to a cervix, a user easily determines an incompetent cervix.

The above-described method may be written as computer programs and may be implemented in general-use digital computers that execute the programs using computer-readable recording media. A structure of data used in the above-described method may be recorded in computer-readable recording media through various members. Examples of the computer-readable recording medium include storage media such as magnetic storage media (e.g., ROM, RAM, USB, floppy disks, hard disks, etc.), optical recording media (e.g., CD-ROMs, or DVDs), etc), and PC interfaces (for example, PCI, PCI-express, and WiFi).

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An ultrasound diagnosis apparatus comprising:
   a probe;
   a pressure measurer comprising one of a variant, a pressure sensor, or a piezo element that measures a pressure value applied from the probe to a cervix;
   a controller that is configured to acquire ultrasound images based on ultrasound data received from the probe;
   wherein the controller is further configured to:
      determine a reference ultrasound image from among the ultrasound images when a contour line of a head bone of a fetus is included in the reference ultrasound image;
      compare the reference ultrasound image with a plurality of ultrasound images which appear after the reference ultrasound image;
      determine whether a cervix line is included in an ultrasound image from among the plurality of ultrasound images that appear after the reference ultrasound image, based on whether a horizontal line, which is not included in the reference ultrasound image, appears in the ultrasound image;
      acquire the measured pressure value as a first pressure value when the cervix line is included in the ultrasound image; and
      calculate a pressure information which includes an arithmetic relationship between the first pressure value and a second pressure value; and
   a display that displays, at a same time, the ultrasound image and the pressure information,
   wherein the second pressure value is previously stored in a memory as a pressure value that is suitable for measuring a cervix line.

2. The ultrasound diagnosis apparatus of claim 1, wherein, the controller is further configured to acquire the ultrasound images from different positions of the probe.

3. The ultrasound diagnosis apparatus of claim 1, wherein the controller is further configured to detect the contour line from the ultrasound image by using at least one selected from a Sobel mask, a Prewitt mask, a Robert mask, and a Canny mask, and determine whether the cervix line is present, based on the contour line.

4. The ultrasound diagnosis apparatus of claim 1, wherein the display displays the pressure information as at least one selected from a letter, a figure, or a color.

5. The ultrasound diagnosis apparatus of claim 1, further comprising an input device that receives the second pressure value from a user.

6. The ultrasound diagnosis apparatus of claim 1, wherein,
   the pressure measurer is the variant, and the variant includes a material that is disposed in front of a transducer of the probe and deformed according to pressure applied through the probe, and
   the pressure measurer measures the pressure value, based on a deformation degree of the material which appears in the ultrasound image and an elastic coefficient of the material.

7. The ultrasound diagnosis apparatus of claim 1, wherein the pressure measurer is the pressure sensor,
   the pressure sensor is disposed in the probe, and
   the pressure measurer measures the pressure value, based on an output of the pressure sensor.

8. The ultrasound diagnosis apparatus of claim 1, wherein, the pressure measurer is the piezo element, and
   the pressure measurer measures the pressure value, based on an electrical signal output from the piezo element.

9. The ultrasound diagnosis apparatus of claim 8, wherein the piezo element is at least one of a plurality of transducers included in the probe.

10. A method of operating an ultrasound diagnosis apparatus, the method comprising:
  measuring a pressure value applied from a probe to a cervix by using one of a variant, a pressure sensor, or a piezo element;
  acquiring ultrasound images based on ultrasound data received from the probe;
  determining a reference ultrasound image from among the ultrasound images when a contour line of a head bone of a fetus is included in the reference ultrasound image;
  comparing the reference ultrasound image with a plurality of ultrasound images which appear after the reference ultrasound image;
  determining whether a cervix line is included in an ultrasound image from among the plurality of ultrasound images which appear after the reference ultrasound image, based on whether a horizontal line, which is not included in the reference ultrasound image, appears in the ultrasound image;
  acquiring the measured pressure value, as a first pressure value when the cervix line is included in the ultrasound image;
  calculating a pressure information which includes an arithmetic relationship between the first pressure value and a second pressure value; and
  displaying, at a same time, the ultrasound image and the pressure information,
  wherein the second pressure value is previously stored in a memory as a pressure value that is suitable for measuring a cervix line.

11. The method of claim 10, wherein,
the acquiring of the ultrasound images comprises acquiring the ultrasound images from different positions of the probe.

12. The method of claim 10, wherein the determining whether the cervix line is included in the ultrasound image comprises:
  detecting the contour line from the ultrasound image by using at least one selected from a Sobel mask, a Prewitt mask, a Robert mask, and a Canny mask; and
  determining whether the cervix line is present, based on the contour line.

13. The method of claim 10, wherein the displaying comprises displaying the pressure information as at least one selected from a letter, a figure, or a color.

14. The method of claim 10, further comprising:
receiving the second pressure value from a user.

15. The method of claim 10, wherein,
the probe includes the variant, and the variant includes a material that is disposed in front of a transducer of the probe and deformed according to pressure applied through the probe, and
the measuring of the pressure value comprises measuring the pressure value, based on a deformation degree of the material which appears in the ultrasound image and an elastic coefficient of the material.

16. The method of claim 10, wherein,
the probe includes the pressure sensor, and
the measuring of the pressure value comprises measuring the pressure value, based on an output of the pressure sensor.

17. The method of claim 10, wherein,
the probe includes the piezo element, and
the measuring of the pressure value comprises measuring the pressure value, based on an electrical signal output from the piezo element.

18. A non-transitory computer-readable storage medium storing a program for executing the method of claim 10.

* * * * *